United States Patent [19]

Faith et al.

[11] Patent Number: 4,743,608

[45] Date of Patent: May 10, 1988

[54] PYRIDONE-PYRIDYL-IMIDAZOLYL AND TRIAZOLYL COMPOUNDS AND THEIR USE AS CARDIOTONIC AGENTS

[75] Inventors: William C. Faith, Ambler; Henry F. Campbell, Lansdale; Donald E. Kuhla, Doylestown, all of Pa.

[73] Assignee: Rorer Pharmaceutical Corporation, Fort Washington, Pa.

[21] Appl. No.: 885,895

[22] Filed: Jul. 15, 1986

[51] Int. Cl.$^4$ .................. A61K 31/345; A61K 31/41; C07D 401/14
[52] U.S. Cl. ..................................... 514/333; 546/256
[58] Field of Search ....................... 546/256; 514/333

[56] References Cited

U.S. PATENT DOCUMENTS

| | | | |
|---|---|---|---|
| 4,004,012 | 1/1977 | Lesher et al. | 546/257 |
| 4,072,746 | 2/1978 | Lesher et al. | 546/257 |
| 4,107,315 | 8/1978 | Lesher et al. | 546/257 |

Primary Examiner—Henry R. Jiles
Assistant Examiner—Zinna Northington
Attorney, Agent, or Firm—James A. Nicholson

[57] ABSTRACT

This invention relates to pyridone-pyridyl-imidazolyl and triazolyl compounds, including methods for increasing cardiac contractility, pharmaceutical compositions including the same and methods for the preparation thereof.

11 Claims, No Drawings

PYRIDONE-PYRIDYL-IMIDAZOLYL AND TRIAZOLYL COMPOUNDS AND THEIR USE AS CARDIOTONIC AGENTS

FIELD OF THE INVENTION

This invention relates to novel imidazolyl and triazolyl compounds bridged to a pyridone ring through a pyridyl moiety at the 2.5-positions of the pyridine ring. These compounds possess useful cardiotonic properties. This invention also relates to the use of said imidazolyl and triazolyl pyridyl pyridone compounds as cardiotonic agents for increasing cardiac contractility, which can be used, for example, for the treatment of congestive heart failure. This invention further relates to pharmaceutical compositions including these same imidazolyl and triazolyl pyridyl-pyridone compounds and the processes for the preparation thereof.

Congestive heart failure is a life-threatening condition in which myocardial contractility is depressed so that the heart is unable to adequately pump blood. Normal pathologic sequelae include decreased cardiac output, venous pooling, increased venous pressure, edema, increased heart size, increased myocardial wall tension, and eventually cessation of contractility.

REPORTED DEVELOPMENTS

Drugs which increase the tone of the heart muscle are described as having positive inotropic activity and are characterized as cardiotonic agents. Digitalis glycosides have long been used to increase myocardial contractility and reverse the detrimental changes seen in congestive heart failure. More recently, dopamine, dobutamine, and amrinone have been used to provide necessary inotropic support for the failing heart.

Cardiotonic agents which are described as having positive inotropic activity include the 5-pyridyl substituted pyridones disclosed in U.S. Pat. Nos. 4,004,012; 4,072,746; 4,107,315; 4,137,233; 4,199,586; 4,271,168; and 4,107,315; in GB 2070606A; and in PCT published Appl. No. PCT/CH81/00023. Other cardiotonic drugs include 2(1H)-pyridone compounds having a phenyl ring attached at the 5-position and which phenyl ring may further be substituted at the 3-or 4-position of the phenyl ring with a 1-imidazolyl group. These are disclosed in U.S. Pat. No. 4,503,061.

SUMMARY OF THE INVENTION

The present invention relates to imidazolyl and triazolyl compounds bridged to a pyridone ring by a pyridyl moiety at the 2,5-positions of the pyridine ring as described by general formula I.

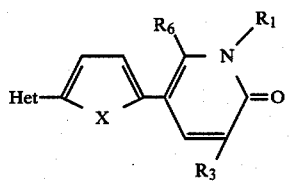

I wherein:
Het is imidazol-1-yl or 1,2,4-triazol-1-yl;
X is —CH=N—or —N=CH—;
$R_1$ and $R_6$ are H or alkyl; and
$R_3$ is H, alkyl, alkoxyalkyl, hydroxyalkyl, halo, cyano, carbamoyl, alkyl carbamoyl, formyl, alkyleneamino or amino; or a pharmaceutically acceptable salt thereof.

It has been found that compounds within the scope of the present invention possess surprising and unexpected positive inotropic activity with a surprisingly high degree of selectivity for their effects on contractile force vs. their effects on heart rate.

This invention relates also to pharmaceutical compositions which are effective in increasing cardiotonic contractility in humans or other animals and which are useful for the treatment of cardiac failure such as congestive heart failure.

DETAILED DESCRIPTION

Certain of the compounds encompassed with the scope of the present invention, and particularly, compounds of the above formula, may exist in enolic or tautomeric forms. All of such forms are considered as being included within the scope of this invention.

The compounds of this invention which have particular usefulness as cardiotonic agents are described by formulae II to V.

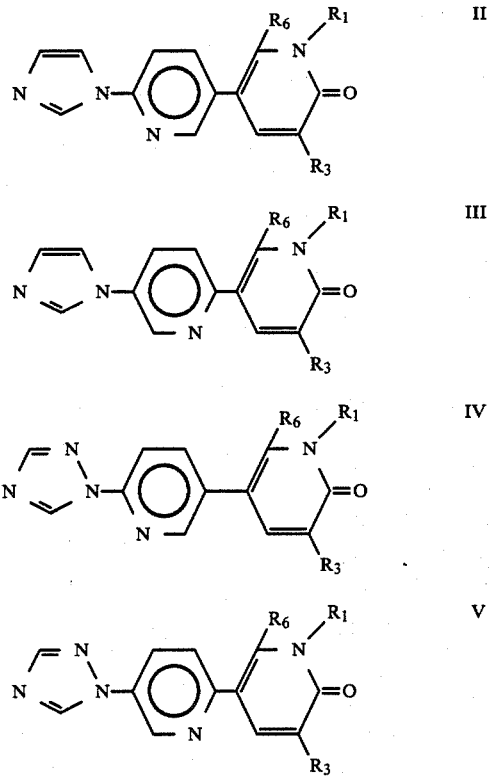

wherein $R_1$, $R_3$ and $R_6$ are as described above.

The compounds of this invention may be useful in the form of the free base, in the form of salts, and as a hydrate. All of such forms are considered as being within the scope of this invention.

As employed above and throughout the disclosure, the following terms, unless otherwise indicated, shall be understood to have the following meanings:

"Alkyl" means a saturated aliphatic hydrocarbon which may be either straight- or branched-chained containing from about one to about 6 carbon atoms.

"Lower alkyl" means an alkyl group as above, having 1 to about 4 carbon atoms.

"Alkyl carbamoyl" means a carbamoyl group substituted by one or two alkyl groups. Preferred groups are the lower alkyl carbamoyl groups.

"Hydroxyalkyl" means an alkyl group substituted by a hydroxy group. Hydroxy lower alkyl groups are preferred and include hydroxymethyl, 2-hydroxyethyl, 2-hydroxypropyl, and 3-hydroxypropyl.

"Alkoxy" means an alkyl oxy group in which "alkyl" is as previously described. Lower alkoxy groups are preferred and include methoxy, ethoxy, n-propoxy, i-propoxy, sec-propoxy, n-butoxy among others.

"Alkoxyalkyl" means an alkyl group as previously described substituted by an alkoxy group as previously described.

N,N-Alkyleneamino means $NR_2$ where -R is alkylene of 1 to about 6 carbon atoms. The preferred groups are the lower alkyleneamino groups which mean amino groups substituted with alkylene groups of 1 to about 4 carbon atoms. The most preferred alkyleneamino group is methyleneamino.

The preferred halo group is cloro.

Preferred compounds of this invention include those compounds of formulae II to V where $R_3$ is cyano.

The more preferred compounds are those of formulae II to V where $R_1$ is hydrogen; $R_3$ is cyano and $R_6$ is lower alkyl, while the most preferred compounds are those of formulae II and IV where $R_6$ is methyl, that is:

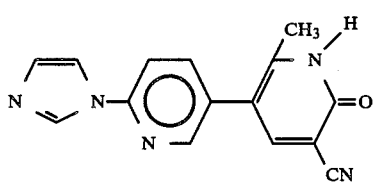

VI

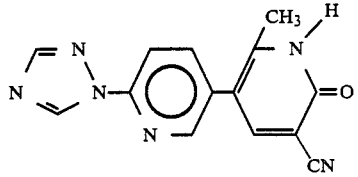

VII

Compounds of this invention may be prepared by the following reaction sequences:

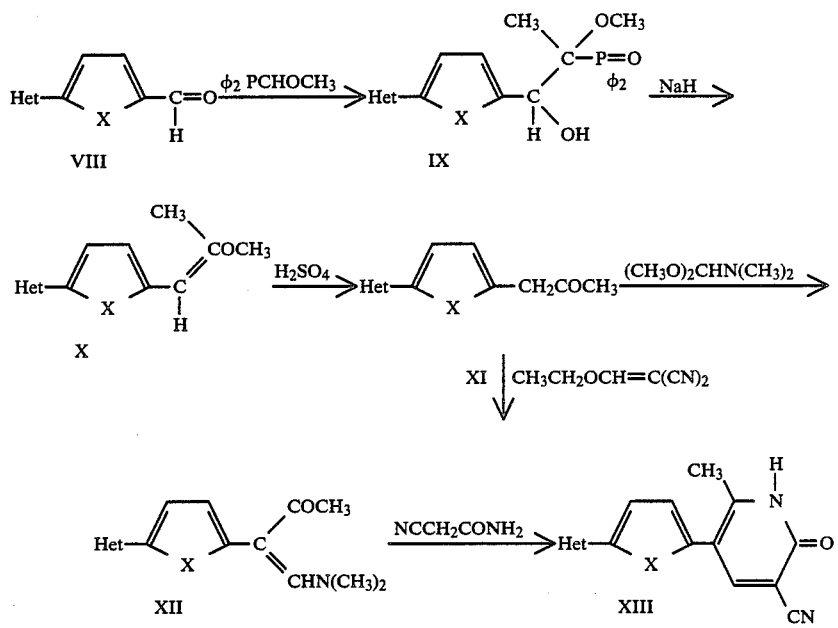

where Het is as described above.

When a 2 or 5-(imidazol-1-yl or 1,2,4-triazol-1-yl)-5 or 2-pyridine carboxaldehyde (VIII) is treated with a lithium derivative of methoxyethyldiphenylphospine oxide, the adduct (IX) is generated. Upon treatment of this adduct with sodium hydride in THF the vinyl ether (X) is prepared. Hydrolysis of the resultant ether with dilute acid (preferably sulfuric or hydrochloric) in THF results in the preparation of the corresponding ketone (XI). Reaction of the ketone with dimethylformamide dimethylacetal (DMF-DMA) with warming followed by treatment, in DMF or the like, with cyanoacetamide in the presence of sodium hydride results in the desired 5-[3 or 2-{6 or 5-(1H-imidazol-1-yl or 1H-1,2,4-triazol-1-yl)} pyridyl]-1,2-dihydro-6-methyl-2-oxo-3-pyridinecarbonitrile XIII.

Reaction of the ketone XI with ethoxymethylenemalononitrile following the procedure of Singh [Heterocycles, 23, 1479 (1985)] also results in the desired compounds of XIII.

Conversion of the cyano group into the other $R_3$ substituents groups may be accomplished by techniques known in the art.

Treatment of the 1-(H)-pyridone compound with a suitable alkylating agent results in the compounds of the present invention wherein $R_1$ is other than hydrogen.

When $R_6$ is hydrogen the starting ketone is reacted with methoxymethyldiphenylphosphine oxide in place of methoxyethyldiphenylphosphine oxide.

The aldehyde starting materials of VIII may be prepared by the following sequence.

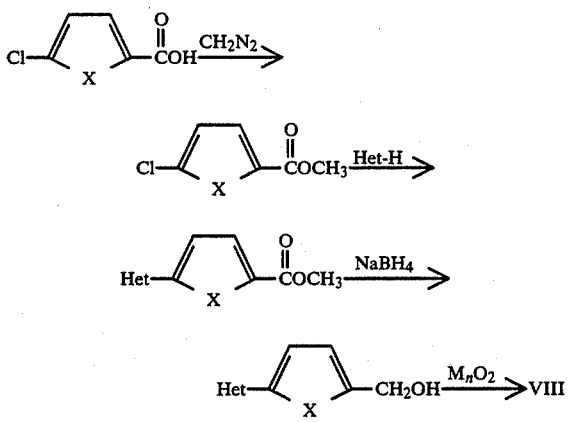

where Het is as described above.

6-chloronicotinic acid and 5-chloropicolinic acid are converted to the methyl esters with diazomethane and condensed with 1H-imidazole or 1H-1,2,4-triazole of formula I under standard technique using sodium hydride in DMF. Reduction of the ester to the alcohol followed by normal oxidation procedures using manganese oxide results in the desired aldehydes of formula VIII.

Acid addition salts are a convenient form for use. In practice, use of the salt form inherently amounts to use of the base form. Acids which can be used to prepare the acid addition salts include preferably those which produce, when combined with the free base, pharmaceutically acceptable salts, that is, salts whose anions are non-toxic to the animal organism in pharmaceutical doses of the salts, so that the beneficial cardiotonic properties inherent in the free base are not vitiated by side effects ascribable to the anions. Although pharmaceutically acceptable salts of said basic compound are preferred, all acid addition salts are useful as sources of the free base form even if the particular salt per se is desired only as an intermediate product as, for example, when the salt is formed only for purposes of purification and identification, or when it is used as an intermediate in preparing a pharmaceutically acceptable salt by ion exchange procedures.

Examples of pharmaceutically acceptable salts within the scope of the invention are those derived from the following acids: mineral acids such as hydrochloric acid, sulfuric acid, phosphoric acid and sulfamic acid; and organic acids such as acetic acid, citric acid, lactic acid, tartaric acid, malonic acid, methanesulfonic acid, ethanesulfonic acid, benzenesulfonic acid, p-toluenesulfonic acid, cyclohexylsulfamic acid, quinic acid, and the like. The corresponding acid addition salts comprise the following: hydrochloride, sulfate, phosphate, sulfamate, acetate, citrate, lactate, tartrate, malonate, methanesulfonate, ethanesulfonate, benzenesulfonate, p-toluenesulfonate, cyclohexylsulfamate and quinate, respectively.

The acid addition salts of the compounds of this invention can be prepared either by dissolving the free base in an aqueous or aqueous alcohol solution or other suitable solvent(s) containing the appropriate acid and isolating the salt by evaporating the solution, or by reacting the free base and acid in an organic solvent, in which case the salt separates directly or can be obtained by concentration of the solution.

The compounds of formula I possess positive inotropic activity and are useful as cardiotonic agents in the treatment of humans and other mammals for cardiac disorders including congestive heart failure. The effectiveness of the compounds of this invention as inotropic agents may be determined by the following pharmacologic tests which evaluate the change in cardiac contractile force upon exposure to a dose of said compounds. The anesthetized dog procedure is a standard test procedure; the inotropic results of this procedure generally correlate with the inotropic activity found in human patients.

Ganglionic-Beta Blocked Anesthetized Dog Procedure

Adult mongrel dogs of either sex weighing 10 to 16 kg are fasted overnight, anesthetized with pentobarbital sodium 35 mg/kg, i.v. intubated, respired with room air using a Harvard respirator, and instrumented surgically to monitor myocardial contractile force, heart rate, arterial pressure, aortic flow and EKG limb lead II. The aforesaid measurements are recorded continuously on a strip chart recorder.

Myocardial contractile force is monitored by a Walton-Brodie strain gauge sutured to the left ventricular myocardium parallel to the left anterior descending coronary artery. Arterial pressure is measured using a fluid-filled catheter attached to a pressure transducer introduced via the right femoral artery and positioned in the thoracic aorta. Mean arterial pressure is determined by electronically clamping the pulsatile pressure signal. Aortic flow is monitored using a precalibrated, noncamulating electromagnetic flow probe positioned around the thoracic aorta. Heart rate is monitored using a cardiotachometer triggered by the QRS complex of the limb lead II EKG. The right femoral vein is cannulated for intravenous infusion of drugs. Body temperature is maintained at 37° C.

Following a 30 min postsurgical stabilization period, control values are recorded. Myocardial depression is induced by ganglionic and beta receptor blockade. Initially, the responsiveness of the autonomic nervous system is assessed by performing a 30 sec bilateral carotid occlusion (BCO). Ten minutes later, a saline solution of isoproterenol 0.3 mg/kg, i.v. is administered to assess beta receptor integrity. Ten minutes after that, a saline solution of mecamylamine 2 mg/kg. i.v. is infused, followed by a saline solution of propranolol 1 mg/kg i.v. plus 0.3 mg/kg/hr. Twenty minutes later, a second BCO is performed to demonstrate ganglionic blockade followed by a second injection of saline isoproterenol 0.3 mg/kg, i.v. to demonstrate beta blockade. Ten minutes later, the test compound or vehicle is administered intravenously in ascending doses at 30 min intervals at 1.5 ml/min in a total volume of 3.5 ml. On completion of the experiment, both BCO and isoproterenol challenges are repeated to verify ganglionic and beta blockade.

The results of the blocked dog test show that compounds of the present invention increase contractile force and heart rate, and aortic blood flow in a dose related manner while maintaining arterial pressure.

Additional test procedures which have been found to be an efficient means for ascertaining the inotropic activity of the compounds of this invention are described below.

Guinea Pig Atria Inotropic Screening Concentrations

Guinea pigs are stunned by a sudden blow to the head; their chests are opened and hearts excised and placed in Kreb's medium (concentrations, mM: NaCl, 118.39; KCl, 4.70; MgSO$_4$, 1.18; KH$_2$PO$_4$, 1.18; NaHCO$_3$, 25.00; glucose, 11.66 and CaCl$_2$, 1.25 gassed with a mixture of 95% O$_2$. Left atria are removed and inserted into warmed (33° C.) double jacketed tissue chambers containing oxygenated Kreb's medium (as above). The upper end of each tissue is attached to a Statham Universal Transducing Cell via a Statham Microscale Accessory. Resting tension on each tissue is set at 1 g and adjusted periodically.

Massive field stimulation is achieved via a pair of platiunum or silver electrodes placed on opposite sides of the tissue. Electrodes are made from 2-gauge silver wire wound into a tight coil approximately 12–14 mm in diameter. Electrodes are connected to a Grass stimulator via a Grass constant current unit. Tissues are driven at 90 pulses per minute with 5 msec duration at current levels 20% greater than threshold for continuous best.

Cumulative concentrations of test drugs are added to the tissue bath at intervals sufficient to allow developed tension to peak at a new level.

The increase in developed tension in each tissue for each compound concentration is measured, and the results are averaged and used to construct cumulative concentration-response curves. Slopes for these regressions calculated via the method of Finney (1971) are compared using Student's t-test The following in vitro method is another means for measuring the inotropic potency of the present compounds. This method is a modification of the enzyme inhibition method reported by Thompson and Appleman (1970) and Thompson et al (1974), and is believed to correlate to in vivo inotropic activity in humans.

Inhibition Of Peak III cAMP Phosphodiesterase Activity

The test compounds are included in media comprising a radioactively labeled substrate ($^3$H-cyclic nucleotide) such as adenosine 3':5'-monophosphate (cyclic AMP) and guanosine-3':5'-nucleotideature isolated from a dog heart. The inhibition of the enzyme hydrolysis of the 5'-nucleotide product of the cNUC-PDEase to the corresponding nucleoside is measured by separating the charged, unhydrolyzed substrate from the uncharged hydrolysis product. Separation may be achieved either chromatographically from the uncharged nucleoside product of the assay with ionexchange resin so that it is not quantitated with the liquid scintillation counter.

Anesthetized Dog Procedure

Male mongrel dogs are anesthetized with pentobarbital (35 mg/kg i.v.) and intubated. Femoral artery and veins are cannulated for measurement of blood pressure and injection of compounds, respectively. A catheter connected to a Statham transducer is inserted into the left ventricle via the right carotid artery for measurement of left ventricular pressure, left ventricular end diastolic pressure and dP/dt. Lead II ECG and heart rate are also monitored. All parameters are measured on a Beckman Dynagraph.

Two additional test procedures which have been found to be an efficient means for ascertaining the inotropic activity of the compounds of this invention are described below.

Conscious Instrumented Dog

Female mongrel dogs (18.0–18.5 kg) are anesthetized with sodium pentobarbital (35 mg/kg i.v., supplemented as necessary during surgery) intubated and connected to a Harvard respirator. The left side of the chest is opened at the fifth intercostal space, and a Konigsberg transducer inserted into the left ventricle through a puncture at the apex and secured. A fluid-filled polyethylene catheter is inserted into the left atrium through a puncture wound and secured for measurement of left atrial pressure. A second fluid-filled catheter is inserted into the aorta for measurement of blood pressure and heart rate and secured to the vessel wall. The two catheters and the Konigsberg transducer cable are passed out of the chest through the seventh intercostal space and advanced subcutaneously to the back of the neck and passed through the skin. The fluid-filled catheters are filled with heparinized 50% dextrose solution, and the chest is closed and evacuated.

The dogs are treated daily post-operatively with 600,000 units of penicillin-procaine i.m. for ten days and with chloramphenicol, 500 mg/kg i.m., every other day for 10 days and allowed at least 7 days recovery before use.

Each dog is trained and acclimated to its environment and the presence of personnel during the experiment.

The dogs are fasted overnight before either intravenous or oral administration of the compound. On a test day, the dog is placed in a sling and connected to a recorder (Gould Instruments or Grass Instruments) for measurement of left ventricular pressure, left ventricular and diastolic pressure, left ventricular dP/dt$_{max}$, blood pressure, heart rate (from the blood pressure signal), and the lead II electrocardiogram. The compound is administered both intravenously and orally (liquid and soft gelatin capsule forms) in different experiments and blood samples were taken for determination of blood levels of the compound.

The compounds of this invention can be normally administered orally or parenterally, in the treatment of cardiac disorders such as heart failure in humans or other mammals.

The compounds of this invention, preferably in the form of a salt, may be formulated for administration in any convenient way, and the invention includes within its scope pharmaceutical compositions containing at least one compound according to the invention adapted for use in human or veterinary medicine. Such compositions may be formulated in a conventional manner using one or more pharmaceutically acceptable carriers or excipients. Suitable carriers include diluents or fillers, sterile aqueous media and various non-toxic organic solvents. The compositions may be formulated in the form of tablets, capsules, lozenges, troches, hard candies, powders, aqueous suspensions, or solutions, injectable solutions, elixirs, syrups and the like and may contain one or more agents selected from the group including sweetening agents, flavoring agents, coloring agents and preserving agents, in order to provide a pharmaceutically acceptable preparation.

The particular carrier and the ratio of inotropic active compound to carrier are determined by the solubility and chemical properties of the compounds, the particular mode of administration and standard pharmaceutical practice. For example, excipients such as lactose, sodium citrate, calcium carbonate and dicalcium phosphate and various disintegratants such as starch, alginic acid and certain complex silicates, together with lubricating agents such as magnesium stearate, sodium lauryl sulphate and talc, can be used in producing tablets. For a capsule form, lactose and high molecular weight polyethylene glycols are among the preferred pharmaceutically acceptable carriers. Where aqueous suspensions for oral use are formulated, the carrier can be emulsifying or suspending agents. Diluents such as ethanol, propylene glycol, glycerin and chloroform and their combinations can be employed as well as other materials.

For parenteral administration, solutions or suspensions of these compounds in sesame or peanut oil or aqueous proplyene glycol solutions, as well as sterile aqueous solutions of the soluble pharmaceutically acceptable salts described herein can be employed. Solutions of the salts of these compounds are especially suited for intramuscular and subcutaneous injection purposes. The aqueous solutions, including those of the salts dissolved in pure distilled water, are also useful for intravenous injection purposes, provided that their pH is properly adjusted, suitably buffered, made isotonic with sufficient saline or glucose and sterilized by heating or by microfiltration.

The dosage regimen in carrying out the methods of this invention is that which insures maximum therapeutic response until improvement is obtained and thereafter the minimum effective level which gives relief. Thus, in general, the dosages are those that are therapeutically effective in increasing the contractile force of the heart or in the treatment of cardiac failure. In general, the oral dose may be between about 0.01 mg/kg and about 50 mg/kg (preferably in the range of 0.1 to 10 mg/kg), and the i.v. dose about 0.005 to about 30 mg/kg (preferably in the range of 0.01 to 3 mg/kg), bearing in mind, of course, that in selecting the appropriate dosage in any specific case, consideration must be given to the patient's weight, general health, age and other factors which may influence response to the drug. The drug may be administered as frequently as is necessary to achieve and sustain the desired therapeutic response. Some patients may respond quickly to a relatively large or small dose and require little or no maintenance dosage. On the other hand, other patients may require sustained dosing from about one to about four times a day depending on the physiological needs of the particular patient. Usually the drug may be administered orally 1 to 4 times per day. It is anticipated that many patients will require no more than about one to about two doses daily.

It is also anticipated that the present invention would be useful as an injectable dosage form which may be administered in an emergency to a patient suffering from acute cardiac failure. Such treatment may be followed by intravenous infusion of the active compound and the amount of compound infused into such a patient should be effective to achieve and maintain the desired therapeutic response.

Compounds of this invention may be prepared by the following reaction sequences.

EXAMPLE 1

2-Imidazolyl-5-pyridinecarboxaldehyde

Step 1. 6-Chloronicotinic acid, methyl ester

An ethereal solution of $CH_2N_2$ (0.1 mole) is added to a suspension of 6-chloronicotinic acid (15 g) in $CH_2Cl_2$ until bubbling ceases. The reaction mixture is stirred overnight, evaporated and dried in vacuo affording the desired product as an off-white solid. M.P.=83°–85° C.

Step 2. 6-(1-H-Imidazol-1-yl)-nicotinic acid, methyl ester

A solution of the methyl ester obtained in Step 1. above (16.29 g) in DMF is added dropwise to a DMF suspension of sodium imidazole [preapred from NaH (4.19 g) and imidazole (6.49 g)] at RT. The reaction mixture is heated to 120° C. for nineteen hours. The cooled reaction mixture is partitioned between water and chloroform, the organic layer separated, washed with water, dried over $Na_2SO_4$, filtered, evaporated, and residual DMF removed under high vacuum yielding the desired product as a tan solid which is recrystalized from methanol. M.P.=200°–202° C.

Step 3. 2-(1H-Imidazol-1-yl)-5-hydroxymethyl pyridine $NaBH_4$ (37.82 g) is added portionwise to a suspension of the imidazolyl ester of Step 2. above (9.98 g) in methanol at about 0° C. The reaction mixture is heated to reflux for 7½ hours, allowed to cool and stand 15 hours. Water (75 ml) is added, and the quenched reaction mixture evaporated, affording a solid residue which is suspended in water, extracted with chloroform, filtered, dried over $Na_2SO_4$, evaporated, and recrystallized ($CHCl_3$), affording the desired product as a white solid. M.P.=124°–126.5° C.

Step 4. 2-(1H-Imidazol-1-yl)-5-pyridinecarboxaldehyde $MnO_2$ (18.17 g) is added to a solution of the hydroxy methyl compound of Step 3. above (6.1 g) in $CHCl_3$, and the resulting reaction mixture heated to reflux for 22 hours, allowed to cool, filtered, and the organic layer evaporated affording the desired product as a white solid. M.P.=136°–137.5° C.

EXAMPLE 2

When the procedure of Example 1 is followed and the 6-chloronicotinic acid is replaced with 5-chloropicolinic acid in Step 1, then the product obtained is 5-(1H-imidazol-1-yl)-2 pyridinecarboxaldehyde.

EXAMPLE 3

When the procedures of Examples 1 and 2 are followed and 1H-imidazole is replaced with 1H-1,2,4-triazole in Step 2, then the products obtained are 2-(1H-1,2,4-triazol-1-yl)-5-pyridine carboxaldehyde and 5-(1H-1,2,4-triazol-1-yl)-2-pyridine carboxaldehyde.

EXAMPLE 4

5-[3-{6-(1H-Imidazol-1-yl)} pyridyl]-1,2-dihydro-6-methyl-2-oxo-3-pyridinecarbonitril Step 1.
2-Diphenylphosphinoyl-2-methoxy-1-[3-{6-(1H-Imidazol-1-yl)} pyridyl] propan-1-ol Methoxyethyldiphenylphosphine oxide (0.70 g, 2.68 mmol) in dry THF (3 ml) is stirred with lithium di-isopropylamide (LDA) [from di-isopropylamine (0.61 g) and n-BuLi (2.2 ml; 2.5M solution in hexane] in THF (12 ml) at 0° C. for 30 min. The mixture is cooled to −78° C. and 2-(imidazol-1-yl)-5-pyridinecarboxaldehyde (0.42 g, 2.44 mmol) in dry THF (7 ml) is added dropwise. The solution is allowed to warm to room temperature over 40 min. and saturated aqueous ammonium chloride solution (30 ml) and ether (40 ml) are added. The aqueous layer is extracted with ether (3×40 ml), and the combined organic layers dried (Na₂SO₄) and evaporated to give a yellow oil. Column chromatography [EtOAc-methanol-triethylamine (19:1:1)] gives 0.36 g of the alcohol.

Step 2. 1-[3-{6-(1H-Imidazol-1-yl)} pyridyl]-2-methoxy-prop-1-ene

A mixture of the alcohol obtained in Step 1. (2.30 g, 5.31 mmol) in 100 ml of THF is stirred with sodium hydride (1.28 g; 50% dispersion in oil) for 1½ hour, then poured into brine (100 ml) and extracted with ether (4×100 ml). The combined organic extracts are dried (Na₂SO₄) and evaporated to give the vinyl ether which is used in the next step without further purification.

Step 3.
1-[3-{6-(1H-Imidazol-1-yl)}pyridyl]-2-propanone

A solution of the vinyl ether (0.90 g, 4.18 mmol) obtained in Step 2. above in 80 ml of THF is treated with 1N H₂SO₄ (19 ml) and stirred at 23° C. for 1 hour. The mixture is poured into H₂O (100ml) which is stirred briefly, made basic with 30% aqueous NaOH, and extracted with ether (5×50 ml). The combined organic layers are dried (Na₂SO₄) and evaporated to produce an oil which is chromatographed [using ethyl acetate-methanol-triethylamine (38:1:1)as the eluent] to give pure propanone as a crystalline solid. M.P.=74°–77° C.

Step 4.
4-(Dimethylamino)-3-[3-{6-(1H-imidazol-1-yl)}pyridyl]-3-buten-2-one

A mixture of the propanone (0.50 g, 2.48 mmol) obtained in Step 3. in 5 ml of dimethylformamide-dimethylacetal (DMF-DMA) is stirred and warmed at 80° C. for 12 hours. The excess DMF-DMA is evaporated under reduced pressure to generate an oil which is chromatographed (using ethyl acetate-methanol (8:2) as the eluent) to give the desired product as a solid. M.P.=117°–122° C.

Step 5.
5-[3-{6-(1H-Imidazol-1-yl)}pyridyl]-1,2-dihydro-6-methyl-2-oxo-3-pyridinecarbonitrile A solution of the above buten-2-one (0.53 g, 2.07 mmol) obtained in Step 4. in 5 ml of DMF is added dropwise to NaH (0.186g; 50% dispersion in oil) and cyanoacetamide (0.19 g, 2.28 mmol) in 5 ml of DMF. The mixture is stirred at 23° C. for 4 hours, quenched with saturated aqueous ammonium chloride, and the resulting precipitate filtered to give the desired product as a solid. M.P.=326°–329° C.

EXAMPLE 5

When the procedure of Example 4 is followed and the 2-(1H-imidazol-1-yl)-5-pyridinecarboxaldehyde of Step 1. is replaced with the aldehydes of Examples 2 and 3 then the corresponding products of Table I below are prepared.

Table I

5-[3-{6-(1H-1,2,4-triazol-1-yl)} pyridyl]-1,2-dihydro-6-methyl-2-oxo-3-pyridinecarbonitrile.
5-[2-{5(1H-imidazol-1-yl)} pyridyl]-1,2-dihydro-6-methyl-2-oxo-3-pyridinecarbonitrile.
5-[2-{5-(1H-1,2,4-triazol-1-yl)} pyridyl]-1,2-dihydro-6-methyl-2-oxo-3-pyridinecarbonitrile.

We claim:

1. A compound of the formula:

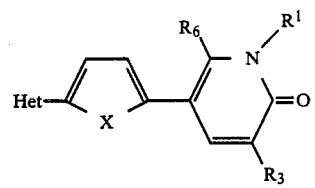

where
Het is imidazol-1-yl or 1,2,4-triazol-1-yl,
x is —CH=N— or —N=CH—;
$R_1$ and $R_6$ are H or lower alkyl; and
$R_3$ is H, lower alkyl, lower alkoxy lower alkyl, hydroxy lower alkyl cyano, carbamoyl, lower alkyl carbamoyl, formyl, —CH₂NH₂ or amino;
or a pharmaceutically acceptable salt thereof.

2. A compound according to claim 1 where $R_3$ is cyano.

3. A compound according to claim 2 where $R_1$ is hydrogen.

4. A compound according to claim 3 where $R_6$ is loweralkyl.

5. A compound according to claim 4 where $R_6$ is methyl.

6. A compound according to claim 5 which is 5-[3-{6-(1H-imidazol-1-yl)} pyridyl]-1,2-dihydro-6-methyl-2-oxo-3-pyridinecarbonitrile.

7. A compound according to claim 5 which is 5-[3-{6-(1H-1,2,4-triazol-1-yl)} pyridyl]-1,2-dihydro-6-methyl-2-oxo-3-pyridinecarbonitrile.

8. A compound according to claim 5 which is 5-[2-{5-(1H-imidazol-1-yl)} pyridyl]-1,2-dihydro-6-methyl-2-oxo-3-pyridinecarbonitrile.

9. A compound according to claim 5 which is 5-[2-{5-(1H-1,2,4-triazol-1-yl)} pyridyl]-1,2-dihydro-6-methyl-2-oxo-3-pyridinecarbonitrile.

10. A method for increasing cardiotonic contractility in a patient requiring such treatment which comprises administering to such patient an effective amount of a compound according to claim 1.

11. A pharmaceutical composition for increasing cardiotonic contractility in a patient requiring such treatment comprising an effective amount of a compound according to claim 1.

* * * * *